United States Statutory Invention Registration [19]

[11] Reg. Number: H270

Hovanec [43] Published: May 5, 1987

[54] CHEMICAL WARFARE SIMULANT

[75] Inventor: Joseph W. Hovanec, Joppa, Md.

[73] Assignee: The United States of America as represented by the Secretary of the Army, Washington, D.C.

[21] Appl. No.: 784,718

[22] Filed: May 5, 1987

[63] Continuation of Ser. No. 582,697, Feb. 23, 1984, abandoned.

[51] Int. Cl.[4] ..... G01N 31/00

[52] U.S. Cl. ..... 436/8

[56] References Cited

U.S. PATENT DOCUMENTS 4,075,006 2/1978 Rinehart ..... 260/455 A

OTHER PUBLICATIONS

Mori et al., Chem. Abstracts, vol. 72, No. 9. Mar. 2, 1970.

*Primary Examiner*—Deborah L. Kyle
*Assistant Examiner*—T. J. Wallen
*Attorney, Agent, or Firm*—Anthony T. Lane; Harold H. Card, Jr.; Edward F. Costigan

[57] ABSTRACT

A chemical 2-(diisopropylamino)ethyl dimethylthiocarbamate as a simulant for use in place of VX nerve gas in decontamination studies.

2 Claims, No Drawings

---

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

CHEMICAL WARFARE SIMULANT

GOVERNMENTAL INTEREST

The invention described herein may be manufactured, used and licensed by or for the Government for governmental purposes without the payment to me of any royalties thereon.

This application is a continuation of Ser. No. 582,697, filed Feb. 23, 1984, now abandoned.

BACKGROUND OF THE INVENTION

1. Field of the Invention

This invention relates to a novel simulator of a chemical warfare agent.

More particularly, this invention relates to a chemical which may be used to simulate nerve gas in an improved manner during decontamination procedures.

2. Description of the Prior Art

Difficulties of a technical and administrative nature prevent the use of nerve gas in research, development, and testing procedures due to the hazards involved. Current safety and security regulations which govern the use of toxic chemical warfare agents preclude most research, development, and testing of nerve gas such as VX in most laboratories. For example, no outdoor testing may be done with the actual nerve gas itself. Thus, in order to facilitate chemical defense research, development, testing and evaluation, it is vital to have an inventory of chemical simulants for such nerve gas for specific purposes. It can be seen where simulants are vital to sustained progress in the improvement of our defensive posture relative chemical warfare. As one can see, simulants are used in every major area of the research operation of chemical warfare agents. They are necessary in every stage of the life cycle of a system from conception through basic research, development, testing, evaluation and training.

To date, the only compound used to mimic the chemical behavior of VX is O-ethyl S-ethyl methylphosphonothiolate. However, the solubility and reactivity of this compound preclude the valid performance study of VX at varying pH levels.

It is known that each of the areas of study in testing and evaluation set their own parameters relative the experimental or operating stages. These parameters dictate what properties are essential for an effective simulant in the areas under study. In the past, experimenters had to use their individual judgement in selecting simulants and, many times, a simulator was a material which was used because it was readily available or because of prior use in another stage of the cycle. Many times, the material used for one specific purpose was not altogether satisfactory for a second specific purpose because of its properties.

There has been a long standing need in the research community of chemical defense for a catalog of compounds which might be used as simulants for specific chemical agents under specific conditions particular decomposition or decontamination. In particular, a search for a simulant of VX under decontamination studies is extremely important.

SUMMARY OF THE INVENTION

It is therefore an object of this invention to provide a simulant for VX nerve gas for use in research, development, evaluation and testing of chemically active liquid decontaminants.

Another object is to provide a simulator of VX which is safe to use but mimics the physical and chemical properties of the cited dangerous toxic agent itself.

Other objects and many of the attendant advantages of this invention will become more apparent to those skilled in the art from a reading of the detailed specification which follows.

In general, the simulator of VX must be liquid, should have a solubility similar to VX, and in solution should be destroyed by oxidation and hydrolysis in a manner and rate similar to VX. Thus the three main properties of a simulant are state, solubility, and reactivity. However, a fourth requirement of a decreased amount of toxicity when compared to VX is highly important.

DESCRIPTION OF THE PREFERRED EMBODIMENT

We have found that the chemical 2-(diisopropylamino)ethyl dimethylthiocarbamate is the preferred stimulant for use in place of VX nerve gas in decontamination studies.

The formula for this simulator is, viz.

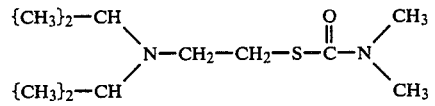

The table I which follows sets forth a comparison of the physical and chemical properties of this simulator as compared to VX.

TABLE I

| | VX | Cited Simulator |
|---|---|---|
| Formula Weight | 267.4 | 232.4 |
| Boiling Point | 298° C. | 320° C. |
| Density-25° C. | 1.008 g/Cm$^3$ | 0.978 g/Cm$^3$ |
| Viscosity-25° C. | 9.96 cP | 9.75 cP |
| Solubility in $H_2O$ - 25° C. | 0.11 M/liter | 0.015 M/liter |
| Hydrolysis | 40 hours @ pH 10 | 60 hours @ pH 10 |
| Toxicity $K_I$ (eel ACHE) | 500,00 $M^{-1}$ $sec^{-1}$ | 17 $M^{-1}$ $sec^{-1}$ |

As seen in Table I, the properties of a necessary simulant in place of VX are shown. It has been found that as a result of this comparison, the simulant of this invention could replace VX in various studies which have to be made. In particular, the simulant besides having properties, which are substantially equivalent to that of VX, is less toxic than the nerve gas and could be used to study decontamination procedures. As shown, the simulant has no significant anti-cholinesterate properties which make it less dangerous. Thus, a low toxicity substitute has been found for VX.

PREPARATION

The simulant 2-(diisopropylamino) ethyl dimethylthiocarbamate is prepared from equimolar amounts of dimethylcarbamayl chloride and 2-(diisopropylamino)ethanethiol hydrochloride. The latter two chemicals are refluxed for about 20 hours in a five-fold molar excess of pyridine. The pyridine is evaporated, and the residue dissolved in chloroform. This solution is washed with dilute sodium hydroxide solution, dried over magnesium sulfate, and the chloroform is evaporated under vacuum. The product is then purified by vacuum distillation, and is collected at 118°–120° C. at 0.55 torr. The distillate, a colorless liquid, was confirmed as a pure compound by nmr spectroscopy, elemental analysis, and gas chromatography.

COMPARISON

REACTION TO AQUEOUS HYPOCHLORITE

In separate experiments, the simulant of this invention and VX nerve gas were reacted with a five-fold molar excess of sodium N, N-dichloroisocyanurate in water. At intervals of two to ten minutes, aliquots of each of the materials were removed and analyzed iodimetrically for active chlorine concentration.

VX nerve gas under the above reaction conditions, consumed chlorine in two kinetically distinct processes. In the first few minutes, there was a rapid consumption of about 1.5 mole equivalent of hypochlorite per mol of VX nerve gas. This was followed by a slower but nearly linear consumption of chlorine over a substantially two hour period.

The chlorine consumption of the simulant of this invention followed a similar two-stage pattern when compared to VX. During the period of 15 minutes to 60 minutes after mixing, their relative chlorine consumptions are within 10 percent of each other.

In comparison, VX is a liquid, so it is the simulant of this invention. VX could never be mimicked by a solid. VX and the cited simulant of this invention have similar solubilities in water and both are pH dependent in similar ways. Once in solution, VX nerve gas may be destroyed by oxidation or hydrolysis, and such is the chemical reactivity of the simulant of this invention.

There has been a long-standing need in the chemical defense research community for a simulant which would satisfactorily mimic the physical and chemical properties of VX. The simulant of this invention has been prepared and its physical properties, slow hydrolysis, and behavior toward hypochlorite make this a suitable simulant for VX. The homologues of the simulant of this invention do not exhibit the desired properties. The cited simulant of this invention may be added to a catalog of compounds which may be used as simulants for specific agents under specific conditions. For example, the simulant of this invention may be used in the testing of chemically active liquid decontaminants in place of VX for research, development, test, and evaluation of new systems.

HYPOCHLORITE OXIDATION

Sodium N, N-dichloroisocyanurate (Fichlor reagent) was used in the comparison of the hypochlorite oxidation reaction. When VX was added to an unbuffered solution of the Fichlor reagent in water at a 5 molar excess relative VX, there was an immediate reaction. Within 1 minute, the VX was destroyed. The data for the simulant in Fichlor exhibited a similar pattern. There was an initial rapid burst of chloring consumption by the simulant which was followed by a slower steady-state consumption. The correlation of VX and simulant relative Kinetics is highly satisfactory for the intended purpose of testing and evaluation of the decontamination procedure.

I claim:

1. In the process of simulating the decontamination of VX nerve gas, the improvement consisting essentially of substituting 2-(diisopropylamino)ethyl dimethylthiocarbonate for said VX in said decontamination.

2. The process of claim 1 wherein said 2-(diisopropylamino)ethyl dimethylthiocarbonate has the following properties, viz.

(a) molecular weight of 232.4,
(b) boiling point of 320° C.,
(c) density of 0.978 g/cm$^3$ at 25° C.,
(d) viscosity of 9.75 cP at 25° C.,
(e) solubility in water of 0.015M at 25° C., and
(f) hydrolysis in $t_{\frac{1}{2}}$ greater than 60 hours at pH10.

* * * * *